United States Patent [19]

Cheetham et al.

[11] Patent Number: 5,219,742

[45] Date of Patent: Jun. 15, 1993

[54] **METHOD OF PRODUCING GAMMA-HYDROXYDECANOIC ACID OR ITS LACTONE BY FEEDING A RICINOLEIC ACID SOURCE TO *SP. ODORUS* OR *RH. GLUTINIS***

[75] Inventors: Peter S. J. Cheetham; Katherine A. Maume, both of Kent, United Kingdom; Johannes F. M. de Rooij, Hilversum, Netherlands

[73] Assignee: Unilever Patent Holdings B.V., Rotterdam, Netherlands

[21] Appl. No.: 544,054

[22] Filed: Jun. 26, 1990

Related U.S. Application Data

[63] Continuation of Ser. No. 78,602, Jul. 28, 1987, abandoned.

[30] Foreign Application Priority Data

Jul. 28, 1986 [GB] United Kingdom ............... 8618351

[51] Int. Cl.$^5$ .......................... C12P 17/04; C12P 7/64
[52] U.S. Cl. .................................. 435/126; 435/134; 435/911
[58] Field of Search ............... 435/123, 126, 134, 244, 435/254, 911

[56] References Cited

U.S. PATENT DOCUMENTS 4,396,715  8/1983  Labows, Jr. et al. ............... 435/126
4,560,656 12/1985  Farbood et al. ..................... 435/146

FOREIGN PATENT DOCUMENTS 100508  6/1985  Japan .
01072  3/1983  PCT Int'l Appl. .

OTHER PUBLICATIONS

Yeasts: Characteristics and Identification, Barnett et al., Cambridge University Press (1986), Entries 388, 389, 391, 392, 396, 397, 427.
Clark et al, "The Encyclopedia of Chemistry", pp. 853-854, 208-210 1957.
Topics in Flavour Research by Jourdain et al, published by Eichhorn (1985).
Okui et al., The Journal of Biochemistry, vol. 54, No. 6, pp. 536-540 (1963).
Biochem. Biophys. Acta., 70:346-348 (1963).
Tahara et al, Agr. Biol. Chem.,36:2585-2587 (1972); 37:2855-2861 (1973).
European Search Report EP 87 30 6559, Apr. 20, 1989.
Tahara, et al., "Neutral Constituents of Volatiles in Cultured Broth of Sporobolomyces odorus", Agr. Biol. Chem. 37 (12), 2855-2861, 1973.

Primary Examiner—Douglas W. Robinson
Assistant Examiner—S. Saucier
Attorney, Agent, or Firm—Cushman, Darby & Cushman

[57] ABSTRACT

Gamma-decalactone is obtained from a source of ricinoleic acid, for example castor oil, by incubation with *Sp. odorus* or *Rh. glutinis*. The product lactone is obtained by lactonising the product hydroxydecanoic acid. The lactone is of value in perfumery and flavors.

10 Claims, No Drawings

METHOD OF PRODUCING GAMMA-HYDROXYDECANOIC ACID OR ITS LACTONE BY FEEDING A RICINOLEIC ACID SOURCE TO SP. ODORUS OR RH. GLUTINIS

This is a continuation of application Ser. No. 07/078,602, filed on Jul. 28, 1987, now abandoned.

FIELD OF INVENTION

This invention relates to the production of gamma-hydroxydecanoic acid from castor oil or its major constituent fatty acid, ricinoleic acid, and its subsequent transformation to optically active gamma-decalactone.

BACKGROUND OF INVENTION

Specific chemicals are widely used in flavour compositions to provide a particular element in the total flavour appreciated by the user. One example of such a chemical is gamma-decalactone which is the lactone of gamma-hydroxydecanoic acid. An example of the use of this material as a flavour is given in UK 743845 (Unilever); this component is also used in perfume compositions. There is a general requirement to produce this component in an efficient procedure.

GENERAL DESCRIPTION

The present invention is directed to a method of producing optically active gamma-hydroxydecanoic acid suitable for conversion to optically active gamma-decalactone wherein a microorganism selected from strains of the group comprising *Sporobolomyces odorus*, *Rhodotorula glutinis* and mixtures thereof is cultured in a nutrient medium containing a ricinoleic acid source under aerobic conditions at a pH from about 3 to about 9 and a temperature from about 15° C. to about 35° C., preferably from about 25° C. to about 30° C., for a sufficient period to produce optically active gamma-hydroxydecanoic acid. The invention optionally includes lactonising the acid for example by the application of heat at acid pH and recovering the gamma-decalactone. The gamma-decalactone can be recovered by standard techniques, e.g. solvent extraction, and purified. The optimum pH for the fermentation is from about 5.5 to about 7.5.

These microorganisms are capable of hydrolysing the castor oil triglyceride and then beta-oxidising ricinoleic acid which is the major fatty acid constituent (80-90%) of the glyceride. These microorganisms can also be used to convert the ricinoleic acid as a substrate either in the form of the substantially pure acid or a constituent of a castor oil hydrolysate obtained by a route not using the two disclosed microorganisms. The culture medium will contain the necessary nutrients for example nitrogen and phosphorus necessary for the growth of the microorganisms.

The microorganisms disclosed herein can beta-oxidise the ricinoleic acid to gamma-hydroxydecanoic acid. This metabolite acid is then available for lactonisation. *Sp. odorus* and *Rh. glutinis* are also capable of hydrolysing castor oil thus allowing this source of ricinoleic acid to be used as a substrate. The applicants describe the use of deposited strains of these species of microorganisms but there is no criticality in the use of these strains and other strains of these species are of general applicability in the process claimed. The process of the invention includes the use of castor oil hydrolysate as the ricinoleic acid source when the hydrolysate is obtained by use of an agent other than those described herein. Examples of these hydrolysis agents are bases, enzymes and other micro-organisms.

The gamma-hydroxydecanoic acid obtained can be lactonised in situ to the desired lactone or recovered and subjected to lactonisation in a separate step.

The prefered culture method operates in the ranges:

| | |
|---|---|
| pH | 3 to 9 |
| Temperature | 15° C. to 35° C. |
| Period | 1 day to 10 days |
| Substrate concentration | 0.3 to 10% by weight |

A concentration in the range 0.5% to 2% will provide a molar conversion of 15% to 40% and is preferred.

Microorganism concentration 1 to 100 g/l of wet cells in innoculum

A period of 1 day is usually sufficient to provide a detectable level of gamma-decalactone. The product concentration will, in general, increase with time and a period of 7 days usually gives a commercially useful concentration. Thus with concentrations of cooked meat medium 2% w/w and castor oil 1% w/w *Rh. glutinis* gave a lactone yield of 880 mg/l and *Sp. odorus* a yield of 1116 mg/l after 7 days.

The product lactone is usually obtained in the range 200 mg/l to 1000 mg/l but can be obtained up to 5,000 mg/l.

The lactonisation is preferably performed by application of heat at an appropirate pH usually by adjusting the hydroxy acid environment to a pH in the range from about 1 to about 7 at a temperature of about 15° C. to about 130° C. for a sufficient period.

A co-oxidant, e.g. decanoic acid, may be present to provide a nutrient source for the micro-organism in addition to the ricinoleic source.

Preferably the microorganism is immobilised on a support, for example k-carrageenan or calcium alginate. Examples of the technique are described in Eu. J. App. Mic & Biotech 15 (1982) pp147-152 and Biotech & Bioeng 19(1977) p387 et seq. Use of immobilisation allows high cell densities to be achieved which lead to increased reaction rates. The cells can be recovered after completion of the process. The cells are partially protected from the substrate and product; this is of benefit if any inhibitory action is present.

One optional process feature is the extraction of the gamma-hydroxydecanoic acid or lactone by a suitable absorbent, for example a non-polar resin, for example Amberlite XAD resins obtainable from BDH of Poole, Dorset, or solvent e.g. Miglyol available from Dynamit Nobel, Witten, West Germany for this product while the fermentation is proceeding. Alternatively, the substrate may be immobilised by standard procedures such as alginate or carrageenan gels. The addition of a triglyceride or fractionated coconut oil fatty acid or triacetin assists the partitioning of the hydroxy acid product from the aqueous layer into the hydrophobic phase. This addition drives the reaction by reducing the concentration of the reaction product at the reaction site. The presence of the hydrophobic solid or liquid phase can also serve to sequester the substrate so that the cells are not exposed to excessively high local concentration of castor oil or ricinoleic acid which may prove toxic to the cells.

Optionally a growth factor, for example riboflavin, nicotinic acid and pantothenic acid, may be included. A particularly favoured carbon source is glycerol which is capable of increasing the yield of the desired lactone especially if *Rh. glutinis* is used. Other alternative carbon sources are sodium acetate and calcium lactate.

An essential feature of the invention is to have at least part of the ricinoleic acid source present at initiation of the incubation. An optional feature of the process is to add the ricinoleic acid source, e.g. castor oil, to the incubation progressively at a rate at which the build-up of inhibitory concentrations of the ricinoleic acid source is avoided while converting substantial amounts on a continuous basis. The incubation of the ricinoleic acid source with the selected micro-organism may be performed in a process in which the micro-organism cells grow and ricinoleic acid source conversion continue in parallel, or a process in which the micro-organism cells are grown and then the conversion process according to the invention is performed in sequence.

There is some loss of the desired product in the exit gasses from the fermenter and the desired lactone can be recovered using an absorbent, for example Tenax Gc, placed in the gas stream.

In addition to the desired hydroxy acid, there will also be small quantities of e.g. C8 and C12 hydroxy acids generated from the ricinoleic acid. Therefore the product lactone may contain homologue lactones corresponding to these acids at low levels. Furthermore metabolites of other fatty acids derived from castor oil may be present. It is to be understood that all these minor products may contribute to the organoleptic properties of the product lactone.

Literature

The preparation of gamma decalactone from castor oil with the aid of specified micro-organisms is disclosed by Fritzsche, Dodge and Olcott Inc in U.S. Pat. No. 4,560,656. These micro-organisms are not those to which the present invention is directed. Subjecting castor oil to treatment by micro-organisms to provide gamma-decalactone is also disclosed in Japanese Kokai 100508/1985 of Kanebo Limited. The use of *Sp. odorus* to prepare gamma-decalactone from sugar substrates is disclosed by Jourdain et al (Topics in Flavour Research 1985 published by Eichhorn).

The present process provides gamma decalactone in useful quantities in an efficient manner.

SPECIFIC DESCRIPTION OF THE INVENTION

Examples of the method will now be given to illustrate but not limit the invention.

EXAMPLE 1

A 3 ml inoculum containing about 10 g (wet weight)-/litre cells of *Rh. glutinis* (NCYC 59 deposited with National Collection of Yeast Cultures, Food Research Institute, Norwich, England) as the micro-organism was added to 100 mls of medium containing 2% w/v cooked meat medium (OXOID CM 81), 2% w/v glucose and 0.02% w/v Tween 80 and 0.5% w/v castor oil and maintained at 28°-30° C. for 7 days.

Samples (5 mls) of the medium were periodically removed aseptically to determine the progress of the process, the samples being lactonised by acidification to pH about 1.5 and heating at 120° C. for 10 minutes. The samples were then extracted with diethylether (5 mls), the organic layer separated and the solvent evaporated, the residue remaining being redissolved in 2 mls ethyl alcohol containing delta-undecalactone (0.04% w/v) as an internal standard and the sample examined by GLC analysis.

After 7 days the fermented material was extracted. Alternatively, following fermentation, the upper castor oil layer, or the cells isolated by sedimentation, can be removed and the acid/lactone present in the castor oil or cells can be extracted as above. In the latter case the solvent also serves to extract acid/lactone present within the cells.

A concentration of 608 mg/l gamma-decalactone was obtained from the fermentation broth representing a yield of 21.3% based on castor oil on the basis of a theoretical maximum yield of about 60%.

The above fermentation can be carried out in a fermenter (L H Fermentation, stoke Poyes, 500 series) maintaining a pH of 7.2, aeration rate 0.51 of air/l.v. fermenter/minute and an agitation rate of 300 r.p.m., temperature 28° C.

EXAMPLE 2

The procedure of Example 1 was followed with a castor oil concentration of 1% w/v in the solution, giving a gamma-decalactone level of 851 mg/l, representing an approximate molar yield of 14.7%.

EXAMPLE 3

The procedure of Example 1 was followed using a castor oil concentration of 5%, but extracting samples with hexane (5 mls) containing 0.5% w/v tetradecane as internal standard and the separated hexane compositions analysed by GLC after 4 and 10 days fermentation, affording yields of 120 and 425 mg/1 respectively. After 1 day the yield was less than 100 mg/l.

EXAMPLE 4

The procedure of Example 2 was followed using *Sp. odorus* (CBS 2636 deposited with Central Bureau Voor Schimmel cultures, Delft, Netherlands) as a micro-organism with a castor oil concentration of 1% w/v in the medium. Gamma-decalactone was observed at concentrations of 388, 564 and 943 mg/l after 3, 5 and 7 days incubation respectively.

EXAMPLE 5

Using the procedure described in Example 1, samples were taken over a 7 day period from a fermentation broth containing 2% w/v cooked meat medium, 1% castor oil and 1% w/v Miglyol 812, using *Rh. glutinis* as the micro-organism. After 7 days the level of gamma-decalactone obtained as described in Example 1 was 377 mg/l.

EXAMPLE 6

A 3 ml inoculum containing about 10g (wet weight)/l cells of *Sp. odorus* was added to 100 mls of medium containing 2% w/v cooked meat medium (Oxoid CM 81), 2% w/v glucose, 0.02% w/v Tween 80 and 0.5% w/v castor oil. Samples were removed as before and lactonised as described before extraction with 5 mls hexane containing 0.5 w/v tetradecane as an internal standard and the hexane extract analysed by GLC, the presence of gamma-decalactone being noted in the first sample after 3 days, its concentration increasing linearly with time until after 7 days a concentration of 950 mg/l was obtained, equivalent to yield of 32% based on castor oil on the basis of a theoretical maximum yield of about 60%.

EXAMPLE 7

Cells of *Rh. glutinis* were cultured in a 100 mls of a nutrient broth containing 2% w/v of a particulate porous polymer to immobilise the micro-organism. After incubation for 2 days, the broth was decanted off and replaced with 2% cooked meat medium and 1% castor oil and incubation continued for a further 7 days, when 762 mg/l of gamma-decalactone were identified in the broth using the extraction procedure as described in Example 1.

EXAMPLE 8

The procedure in Example 7 was followed using 2% beef extract in place of the cooked meat medium. A level of 1031 mg/l gamma-decalactone was identified after 7 days incubation.

EXAMPLE 9

The procedure of example 2 was followed, with the addition of 1% w/v of glass beads (1.5–2 mm diameter) in the nutrient to immobilise the micro-organism. After 7 days incubation a concentration of 1,118 mg/l of gamma-decalactone was obtained, representing a yield of 19.6% based on castor oil on the basis described.

EXAMPLE 10

The procedure in Example 1 was followed, with the addition of 2% w/v Amberlite XAD resin as sequestrant to the broth. 448 mg/l of gamma-decalactone were extracted after 7 days incubation and 199 mg/1 were obtained after only 2 days incubation. The resin was separated from the broth, washed in distilled water and extracted with hexane as described in Example 6.

EXAMPLE 11

The process of Example 6 was repeated with the microorganism cells immobilised on k-carrageenan. A 2% dry w/v aqueous solution of k-carrageenan was prepared by centrifuging the culture broth at about 10,000 revolutions per minute for 15 minutes at 20° C., at a 4:1 w/v level. The cell-carrageenan slurry was then extruded dropwise into a 0.1M solution of potassium chloride to gel the carrageenan and immobilise the cells. This procedure is described by S. Takamatsu et al in European Journal of Applied Microbiology and Biotechnology 15 (1982) pp 147–152.

*Rh. glutinis* was cultured with castor oil and ricinoleic acid in separate media. *Sp. odorus* was cultured with ricinoleic acid. After five days the yields of gamma-decalactone were:

| | |
|---|---|
| Castor oil/Rh glutinis | 153.5 mg/l |
| Ricinoleic acid/Rh glutinis | 154.3 mg/l |
| Ricinoleic acid/Sp odorus | 518 mg/l |

An alternative support is provided by calcium alginate using the procedure described by M Kierstam et al in Biotechnology & Bioengineering 19(1977) p.387 et seq.

The free acid was obtainable from each of the examples as its methyl ester by GLC methods using a packed column containing 10% SP02330 on 100/120 mesh Chromosorb AW (Supelcolac) in a 2 metre column 0.4 cm in diameter. Details of the further extraction may be obtained by reference to Standard Methods for Analysis of Oils, Fats and Derivatives, 6th Edition, Method II D25 (UPAC Methodology Pergamon Press Oxford.

We claim:

1. A method of producing optically active gamma-hydroxydecanoic acid suitable for conversion to optically active gamma-decalactone comprising: culturing a microorganism selected from the group consisting of *Sporobolomyces odorus, Rhodotorula glutinus* and mixtures thereof in a nutrient medium containing a ricinoleic acid source under aerobic conditions at a pH from about 3 to about 9 and a temperature from about 15° C. to about 35° C. for a sufficient period to produce at least 200 mg of optically active gamma-hydroxydecanoic acid per liter of incubation medium and recovering the product.

2. The method according to claim 1 wherein the ricinoleic acid source is ricinoleic acid, castor oil, castor oil hydrolysate or a mixture thereof.

3. The method according to claim 1 or 2 wherein the microorganism is immobilised on a support.

4. The method according to claim 3 wherein the support comprises carrageenan or alginate gels.

5. The method according to claim 1 wherein the gamma-hydroxydecanoic acid is lactonised in situ to produce gamma-decalactone.

6. The method according to claim 1 wherein the product acid is lactonised by the application of heat at an appropriate pH.

7. The method according to claim 6 wherein the lactonisation is achieved by adjusting the pH to acid and the temperature from about 15° C. to about 130° C.

8. The method according to claim 1 wherein the fermentation is carried out in the presence of a sequestrant.

9. The method according to claim 8 wherein the sequestrant comprises a particulate porous polymer or a water immiscible liquid phase.

10. The method according to claim 1 wherein the ricinoleic acid source is added progressively to the incubation at a rate maintaining its concentration below inhibitory levels.

* * * * *